(12) United States Patent
Dimmer

(10) Patent No.: US 6,812,842 B2
(45) Date of Patent: *Nov. 2, 2004

(54) SYSTEM FOR EXCITATION OF A LEADLESS MINIATURE MARKER

(75) Inventor: Steven C. Dimmer, Bellevue, WA (US)

(73) Assignee: Calypso Medical Technologies, Inc., Seattle, WA (US)

( * ) Notice: Subject to any disclaimer, the term of this patent is extended or adjusted under 35 U.S.C. 154(b) by 166 days.

This patent is subject to a terminal disclaimer.

(21) Appl. No.: 10/027,675

(22) Filed: Dec. 20, 2001

(65) Prior Publication Data

US 2003/0122653 A1 Jul. 3, 2003

(51) Int. Cl.[7] .............................................. G08B 13/14
(52) U.S. Cl. ................................ 340/572.4; 340/572.5; 340/573.1
(58) Field of Search ........................... 340/572.1, 572.4, 340/572.5, 573.1

(56) References Cited

U.S. PATENT DOCUMENTS

| | | | |
|---|---|---|---|
| 3,752,960 | A | 8/1973 | Walton |
| 3,967,161 | A | 6/1976 | Lichtblau |
| 4,017,858 | A | 4/1977 | Kuipers |
| 4,023,167 | A | 5/1977 | Wahlstrom |
| 4,123,749 | A | 10/1978 | Hartmann et al. |
| 4,160,971 | A | 7/1979 | Jones et al. |
| 4,260,990 | A | 4/1981 | Lichtblau |
| 4,466,075 | A | 8/1984 | Groch et al. |
| 4,633,250 | A | 12/1986 | Anderson |
| 4,642,786 | A | 2/1987 | Hansen |
| 4,737,794 | A | 4/1988 | Jones |
| 4,795,995 | A | 1/1989 | Eccleston |
| 4,849,692 | A | 7/1989 | Blood |
| 4,945,305 | A | 7/1990 | Blood |
| 5,050,608 | A | 9/1991 | Watanabe et al. |

(List continued on next page.)

FOREIGN PATENT DOCUMENTS

| | | |
|---|---|---|
| EP | 0 719 420 B1 | 11/1999 |
| EP | 1 034 738 | 9/2000 |

(List continued on next page.)

OTHER PUBLICATIONS

Hsiao, K., "Fast Multi–Axis Tracking of Magnetically–Resonant Passive Tags: Methods and Applications," Feb. 2001, Massachusetts Institute of Technology, Dept. of Electrical Engineering and Computer Science.

International Search Report dated Jan. 24, 2003, PCT Application No. PCT/US/29390.

Primary Examiner—Thomas J Mullen, Jr.
(74) Attorney, Agent, or Firm—Perkins Coie LLP

(57) ABSTRACT

A system for generating a pulsed excitation field for excitation of a leadless marker assembly. One aspect of the system comprises a source generator assembly having a power supply, an energy storage device, a switching network and a source coil interconnected and configured to deliver a pulsed magnetic excitation signal waveform. The power supply is configured to deliver power to energize the energy storage device. The switching network is configured to: direct electrical current through the source coil; alternately switch between a first on position and a second on position; switch to an off position to prevent energy transfer from the energy storage device to the source coil; alternately transfer stored energy from the energy storage device to the source coil and to transfer stored energy from the source coil back to the energy storage device; and the source coil being coupled to the switching network to generate a pulsed excitation signal.

27 Claims, 5 Drawing Sheets

U.S. PATENT DOCUMENTS

| | | | |
|---|---|---|---|
| 5,095,224 A | * 3/1992 | Renger | 327/110 |
| 5,099,845 A | 3/1992 | Besz et al. | |
| 5,142,292 A | 8/1992 | Chang | |
| 5,188,368 A | 2/1993 | Ryan | |
| 5,198,877 A | 3/1993 | Schulz | |
| 5,221,269 A | 6/1993 | Miller et al. | |
| 5,240,011 A | 8/1993 | Assa | |
| 5,325,873 A | 7/1994 | Hirschi et al. | |
| 5,377,678 A | 1/1995 | Dumoulin et al. | |
| 5,397,329 A | 3/1995 | Allen | |
| 5,411,026 A | 5/1995 | Carol | |
| 5,417,210 A | 5/1995 | Funda et al. | |
| 5,425,382 A | 6/1995 | Golden et al. | |
| 5,446,548 A | 8/1995 | Gerig et al. | |
| 5,453,686 A | 9/1995 | Anderson | |
| 5,515,853 A | 5/1996 | Smith et al. | |
| 5,526,812 A | 6/1996 | Dumoulin et al. | |
| 5,528,651 A | 6/1996 | Leksell et al. | |
| 5,546,951 A | 8/1996 | Ben-Haim | |
| 5,558,091 A | 9/1996 | Acker et al. | |
| 5,568,809 A | 10/1996 | Ben-haim | |
| 5,572,999 A | 11/1996 | Funda et al. | |
| 5,617,857 A | 4/1997 | Chader et al. | |
| 5,622,170 A | 4/1997 | Schulz | |
| 5,622,187 A | 4/1997 | Carol | |
| 5,629,967 A | 5/1997 | Leksell et al. | |
| 5,630,431 A | 5/1997 | Taylor | |
| 5,645,065 A | 7/1997 | Shapiro et al. | |
| 5,680,106 A | 10/1997 | Schrott | |
| 5,681,326 A | 10/1997 | Lax | |
| 5,727,552 A | 3/1998 | Ryan | |
| 5,745,545 A | 4/1998 | Hughes | |
| RE35,816 E | 6/1998 | Schulz | |
| 5,764,052 A | * 6/1998 | Renger | 324/258 |
| 5,779,638 A | 7/1998 | Vesely et al. | |
| 5,797,849 A | 8/1998 | Vesely et al. | |
| 5,805,661 A | 9/1998 | Leksell et al. | |
| 5,815,076 A | * 9/1998 | Herring | 340/572.5 |
| 5,817,022 A | 10/1998 | Vesely | |
| 5,820,553 A | 10/1998 | Hughes | |
| 5,823,192 A | 10/1998 | Kalend et al. | |
| 5,828,770 A | 10/1998 | Leis et al. | |
| 5,830,144 A | 11/1998 | Vesely | |
| 5,868,673 A | 2/1999 | Vesely | |
| 5,868,675 A | 2/1999 | Henrion et al. | |
| 5,879,357 A | 3/1999 | Heaton et al. | |
| 5,902,238 A | 5/1999 | Golden et al. | |
| 5,902,310 A | 5/1999 | Foerster et al. | |
| 5,913,820 A | 6/1999 | Bladen et al. | |
| 5,923,417 A | 7/1999 | Leis | |
| 5,987,349 A | 11/1999 | Schulz | |
| 6,015,390 A | 1/2000 | Krag | |
| 6,019,725 A | 2/2000 | Vesely et al. | |
| 6,026,818 A | 2/2000 | Blair et al. | |
| 6,049,587 A | 4/2000 | Leksell et al. | |
| 6,052,477 A | 4/2000 | Wang et al. | |
| 6,061,644 A | 5/2000 | Leis | |
| 6,064,904 A | 5/2000 | Yanof et al. | |
| 6,067,465 A | 5/2000 | Foo et al. | |
| 6,094,007 A | 7/2000 | Faul et al. | |
| 6,097,994 A | 8/2000 | Navab et al. | |
| 6,144,875 A | 11/2000 | Schweikard et al. | |
| 6,173,715 B1 | 1/2001 | Sinanan et al. | |
| 6,198,963 B1 | 3/2001 | Haim et al. | |
| 6,239,724 B1 | 5/2001 | Doron et al. | |
| 6,363,940 B1 | 4/2002 | Krag | |
| 6,371,379 B1 | 4/2002 | Dames | |
| 6,401,722 B1 | 6/2002 | Krag | |
| 6,474,341 B1 | 11/2002 | Hunter et al. | |
| 2003/0088178 A1 | * 5/2003 | Owens et al. | 600/420 |

FOREIGN PATENT DOCUMENTS

| | | |
|---|---|---|
| WO | WO 88/08282 | 11/1988 |
| WO | WO 95/33519 | 12/1995 |
| WO | WO 96/08208 A1 | 3/1996 |
| WO | WO 9608999 | 3/1996 |
| WO | WO 97/36192 | 10/1997 |
| WO | WO 97/48438 | 12/1997 |
| WO | WO 98/30166 | 7/1998 |
| WO | WO 99/17133 | 4/1999 |
| WO | WO 99/27839 | 6/1999 |
| WO | WO 99/30182 | 6/1999 |
| WO | WO 99/35966 | 7/1999 |
| WO | WO 99/58055 | 11/1999 |
| WO | WO 99/58065 | 11/1999 |
| WO | WO 00/24332 | 5/2000 |
| WO | WO 00/51514 | 9/2000 |
| WO | WO 01/34049 | 5/2001 |
| WO | WO 01/54765 A2 | 8/2001 |
| WO | WO 02/19908 A1 | 3/2002 |
| WO | WO 02/100485 | 12/2002 |

* cited by examiner

SYSTEM FOR EXCITATION OF A LEADLESS MINIATURE MARKER

TECHNICAL FIELD

This invention relates to systems for activating miniature markers, and more particularly to systems for excitation of resonating miniature marker assemblies for use in locating the markers in three-dimensional space.

BACKGROUND OF THE INVENTION

Systems have been developed to activate and detect remote activatable marker assemblies positioned, as an example, in or on a selected item or object. The markers generate a signal used to detect the presence of the marker. Many of the activatable markers are hard-wired to a power source or other equipment external from the object. Other systems have been developed that utilize resonating leadless markers, also referred to as wireless active markers, positionable at or near a selected target. These wireless active markers are typically activated or energized by a remote excitation source that generates a strong continuous excitation signal. Accordingly, the markers generate a detectable marker signal that must be distinguished from the strong continuous excitation signal and then analyzed in an effort to try to accurately determine the target's location. The process of distinguishing a weak marker signal from the strong continuous excitation signal, while maintaining sufficient accuracy for determining the marker's location, has proven to be very difficult.

Other systems have provided detection of leadless markers to determine a two-dimensional proximity (e.g., X, Y coordinates) to detectors for use with game boards, surgical tag detection devices, and medical tube placement verification systems. In the case of the game boards, a unique game piece with a resonator of a predetermined frequency is moved across the game board, and the X and Y location ordinates of the game piece relative to the game board are displayed so the players can determine the general location of the game piece on the game board. U.S. Pat. No. 5,853,327 to Gilboa identifies that the X, Y coordinates, as a function of amplitude or phase, may be determined experimentally for a given game board design. Additionally, Z distance away from the game board may be determined to a sufficient accuracy for game use by the strength of the signal above the game board provided that the signal is not a strong function of the X and Y locations. U.S. Pat. No. 5,188,368 to Ryan provides a system for determining in two dimensions which individual square of a chess board a particular chess piece is on during a chess game. The system disclosed by Ryan does not determine the Z direction.

In the case of the surgical tag and detection device, U.S. Pat. No. 6,026,818 to Blair discloses surgical devices, such as sponges, that have activatable resonator tags thereon. A probe with an interrogation ring is provided that can be scanned over an area of a patient after surgery to determine if any surgical devices having the resonator tags have been left behind. Therefore, the detection device of Blair is only detecting the existence or proximity of a surgical tag with the interrogation ring, rather than the actual location of the activatable tags.

In the case of the medical tube placement verification device, U.S. Pat. No. 5,325,873 to Hirschi et al. teaches a system that detects the general position of an object within a body of tissue. The detection system includes a resonant circuit attached to the object and a separate detection probe having a visual display indicating the direction which the probe should be moved to center the detection probe over the object.

The systems of the above patents activate the markers with a pulsed excitation signal generated by driving an untuned source coil with either a unipolar polarity to produce a wide band impulse function or a bipolar polarity to create a waveform that more closely matches the desired resonant frequency of the marker. The required levels of magnetic excitation for the markers in the above patents are relatively low such that the excitation energy in the source coil is substantially consumed after each pulse due to the pulse circuitry resistive losses. The source coils are driven by linear amplifiers, and in one case by linear amplifiers at both ends of the coil, and by a simple pulse network that energizes the coil and extinguishes resistively. The amplitude of the pulsed excitation signal required for these applications is relatively low since either the resonator circuit to be located is of a large size, the volume in which the resonator must be located is relatively small, or the accuracy requirements locating the resonator are quite low. Accordingly, the existing systems are not suitable for use in many situations wherein highly accurate determinations of the marker's location in three-dimensional space are required. The existing systems may also not be suitable for use with efficient, high-energy systems for energizing the marker assemblies so as to provide a sufficient marker signal for use in determining the location of the marker in three-dimensional space relative to remote sensors.

Other systems have been developed for proximity detection of resonator tags for Electronic Article Surveillance (EAS) systems. The requirements for EAS systems are to detect the presence of a security tag within a six-foot wide aisle using one antenna assembly for both excitation and detection of the tag within the aisle. Some EAS systems utilize tuned resonant excitation source coil drive circuitry for pulsed resonator tag operation. As an example, U.S. Pat. No. 5,239,696 to Balch et al. discloses a linear amplifier using current feedback linear power amplifiers to drive an excitation source tuned to resonant coils for use in pulsed EAS systems. The current feedback is used to adjust the linear amplifier's drive current level provided to the tuned excitation source coil load. The current feedback is also used to provide for a relatively constant current drive for exciting resonant EAS tags in the field. The source coil is tuned to allow for use of a simple, low voltage linear amplifier circuit design. The source coil current pulse waveform is determined by the summation of the sinusoidal control signal and the drive current feedback signal input to the linear amplifier.

U.S. Pat. No. 5,640,693 to Balch et al. discloses the use of linear power amplifiers to drive tuned excitation source coils for use in pulsed EAS systems. An apparatus for switching power to a linear amplifier is provided to turn to an "on" state and an "off" state used to control the output drive pulse burst of the tuned excitation source coils. Balch et al. '693 also identifies that linear amplifiers which generate drive signals for a tuned source coil since linear amplifiers are typically only about thirty to forty percent efficient. The inherent inefficiency of the linear amplifier drive is improved by switching the amplifier power "on" and "off" at the same time that the pulse control input signal to the power supply is switched "on" and "off" position.

U.S. Pat. No. 5,815,076 to Herring teaches one of more damping circuits provided in series with excitation source coils and used to promote rapid dampening of the pulsed excitation interrogation signals at the end of each signal pulse. Providing the switchable damping circuits in series with the antenna increases the power dissipation of the device during pulse delivery due to added damping circuit switch resistance in the antenna current path.

The above systems employ a resonator circuit energized with a pulsed excitation signal and the resonator response signal is measured with sensing coils. The amplitude of the pulsed excitation signal required for these applications is relatively low since either the resonator circuit to be located is of a large size, the volume in which the resonator must be located is relatively small, or the accuracy requirements locating the resonator are quite low.

SUMMARY OF THE INVENTION

Under one aspect of the invention, a system is provided for generating a pulsed magnetic field for excitation of a leadless marker assembly. The system includes a source generator assembly having a power supply, an energy storage device, a switching network and an untuned source coil interconnected and configured to deliver a pulsed magnetic excitation signal waveform. In one embodiment, the waveform can be configured to contain sufficient energy at the selected leadless marker resonant frequency to energize the marker sufficiently above the ambient environment background noise. The power supply can be configured to deliver power to energize the energy storage device. The switching network can be configured to direct electrical current through the source coil to generate a pulsed magnetic field; alternately switch between a first "on" position and a second "on" position; alternately switch between the first and second "on" positions, switch to an "off" position to prevent energy transfer from the energy storage device to the source coil; alternately transfer stored energy from the energy storage device to the source coil and to transfer stored energy from the source coil back to the energy storage device when switching between the first and second "on" positions; and the untuned source coil being coupled to the switching network to generate a pulsed excitation signal.

Other embodiments of the invention can have other features. Other embodiments are directed toward methods of energizing a leadless marker assembly.

DETAILED DESCRIPTION

In the following description, certain specific details are set forth in order to provide a thorough understanding of various embodiments of the invention. However, one skilled in the art will understand that the invention may be practiced without these details. In other instances, well-known structures associated with magnetic excitation systems, resonating markers, and activators have not been shown or described in detail to avoid unnecessarily obscuring the description of the embodiments of the invention.

FIGS. 1–7 illustrate a system and components for generating an excitation signal for activating a resonating marker assembly and locating the marker in three-dimensional space in accordance with embodiments of the present invention. Several of the components described below with reference to FIGS. 1–7 can also be used in systems for performing methods in accordance with aspects of the present invention. Therefore, like reference numbers refer to like components and features throughout the various figures.

Figure 1:
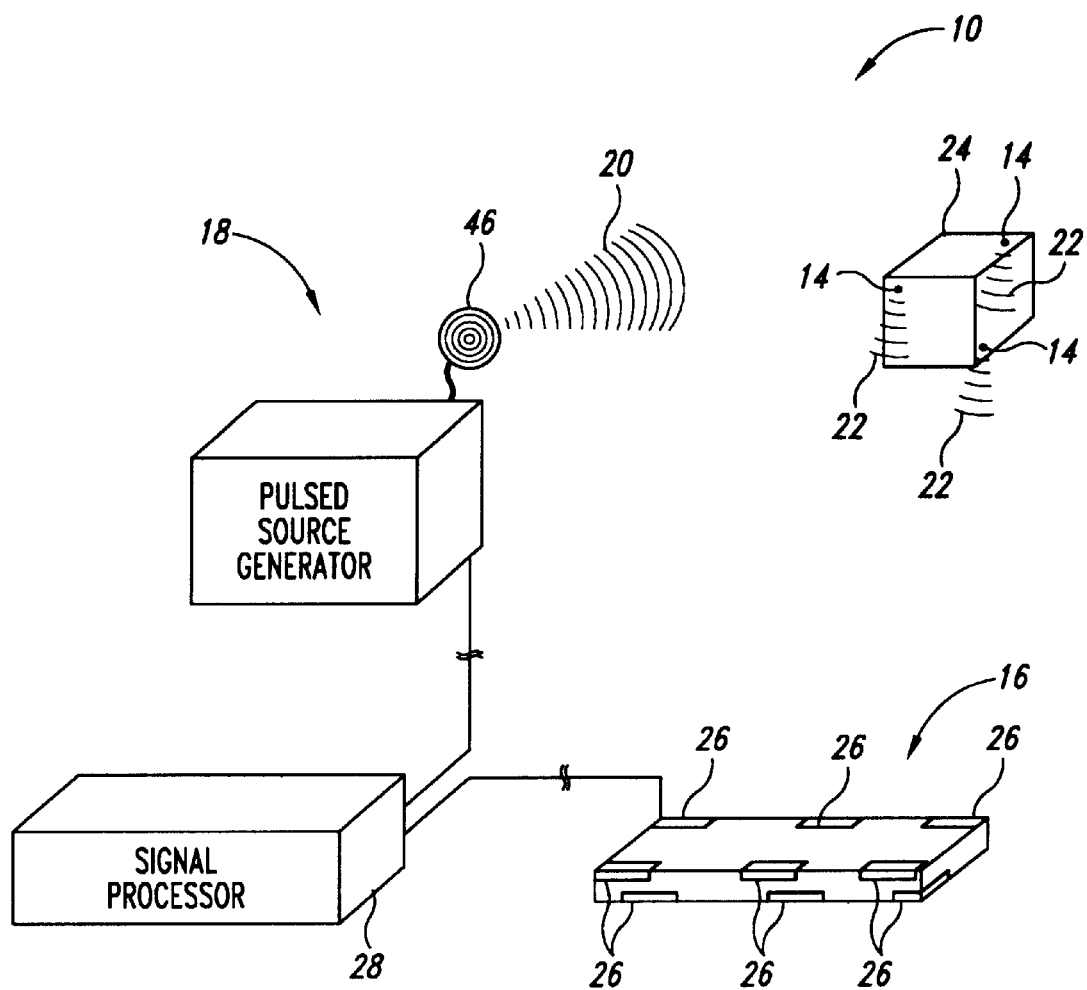
FIG. 1 is a schematic isometric view of a system for pulsing and locating leadless markers in accordance with an embodiment of the present invention.
Figure 2:
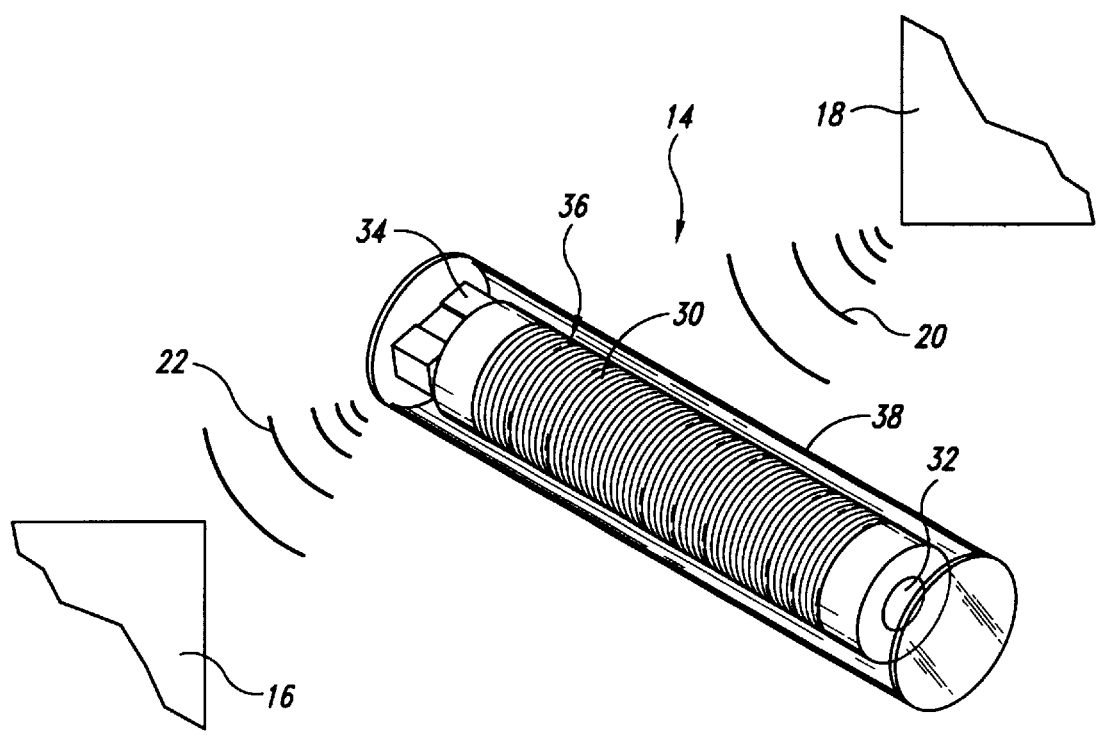
FIG. 2 is an isometric view of an embodiment of an implantable miniature resonating marker assembly usable in the system of FIG. 1.

FIG. 1 is a schematic isometric view of a system 10 for pulsing and locating one or more leadless resonating marker assemblies 14 in three-dimensional space relative to a sensor array 16 in accordance with one embodiment of the present invention. The system 10 includes a pulsed source generator 18 that generates a pulsed magnetic excitation field or signal 20 that energizes the marker assemblies 14. The energized marker assemblies 14 generate a measurable marker signal 22. In the illustrated embodiment, the marker assemblies 14 are positioned in or on a selected object 24 in a known orientation relative to each other. The marker signals 22 are measured by a plurality of sensors 26 in the sensor array 16. The sensors 26 are coupled to a signal processor 28 that utilizes the measurement of the marker signals 22 from the sensors 26 to calculate the location of each marker assembly 14 in three-dimensional space relative to a known frame of reference, such as the sensor array 16.

In the illustrated embodiment, as discussed in greater detail below, the pulsed source generator 18 is configured to generate the pulsed excitation signal 20 until one or more marker assemblies 14 have been sufficiently energized to generate the marker signals 22 and the pulsed source generator 18 is switched off. Once the pulsed source generator 18 is switched off, the excitation signal 20 terminates and is not measurable. Accordingly, the sensors 26 in the sensor array 16 will receive only the marker signals 22 without any interference or magnetic field distortion induced by the excitation signal 20. Termination of the excitation signal 20 occurs before a measurement phase in which marker signals 22 are measured. Such termination of the excitation signal before the measurement phase when the energized marker assemblies 14 are generating the marker signals 22 allows for a sensor array 16 of increased sensitivity that can provide data of a high signal to noise ratio to the signal processor 28 for extremely accurate determination of the three-dimensional location of the marker assemblies 14 relative to the sensor array or other frame of reference.

The miniature marker assemblies 14 in the system 10 of the illustrated embodiment are inert, activatable assemblies that can be excited to generate a signal at a resonant frequency measurable by the sensor array 16 remote from the target 24. In one embodiment, the miniature marker assemblies 14 have, as one example, a diameter of approximately 2 mm and a length of approximately 5 mm, although other marker assemblies can have different dimensions. An example of the marker detection system is described in detail in co-pending U.S. patent application Ser. No. 09/877,498, titled GUIDED RADIATION THERAPY SYSTEM, filed Jun. 8, 2001, which is incorporated herein in its entirety by reference thereto.

The illustrated marker assembly 14 includes a coil 30 wound around a ferromagnetic core 32 to form an inductor.

The inductor is connected to a capacitor 34, so as to form a signal element 36. Accordingly, the signal element 36 is an inductor (L) capacitor (C) resonant circuit. The signal element 36 in one embodiment is enclosed and sealed in an encapsulation member 38 made of plastic, glass, or other inert material. The illustrated marker assembly 14 is a fully contained and inert unit that can be used, as an example, in medical procedures in which the marker assembly is secured on and/or implanted in a patient's body.

Other marker assemblies 14 are described in detail in co-pending U.S. patent application Ser. No. 09/954,700, titled MINIATURE RESONATING MARKER ASSEMBLY, filed Sep. 14, 2001, which is also incorporated herein in its entirety by reference thereto. Other leadless marker assemblies 14 that may be used are described in detail in U.S. patent application Ser. No. 09/078,982, titled SYSTEM AND METHOD FOR BRACKETING AND REMOVING TISSUE, filed May, 14, 1998, now U.S. Pat. No. 6,363,940; PCT Application No. PCT/US00/31667 titled SYSTEMS AND METHODS FOR LOCATING AND DEFINING A TARGET LOCATION WITHIN A HUMAN BODY, filed Nov. 17, 2000; and PCT/US00/31673, titled SYSTEMS AND METHODS FOR STABILIZING A TARGET LOCATION WITHIN A HUMAN BODY, filed Nov. 17, 2000, all of which are incorporated herein in their entireties by reference thereto.

The marker assembly 14 is energized, and thus activated, by the magnetic excitation field or signal 20 generated by the pulsed source generator 18 such that the marker's signal element 36 generates the measurable marker signal 22. The strength of the measurable marker signal 22 is high relative to environmental background noise at the marker resonant frequency, thereby allowing the marker assembly 14 to be precisely located in three-dimensional space relative to the sensor array 16.

The pulsed source generator 18, in one embodiment, is adjustable to generate a pulsed magnetic field 20 having a waveform that contains energy at selected frequencies that substantially match the resonant frequency of the specifically tuned marker assembly 14. When the marker assembly 14 is excited by the magnetic field 20, the signal element 36 generates the response marker signal 22 containing frequency components centered at the marker's resonant frequency. After the marker assembly 14 is energized for a selected time period, the pulsed source generator 18 is switched to the "off" position so the pulsed excitation signal 20 is terminated and provides no measurable interference with the marker signal 22 as received by the sensor array 16.

The marker assembly 14 is constructed to provide an appropriately strong and distinct signal by optimizing marker characteristics and by accurately tuning the marker assembly to a predetermined frequency. Accordingly, multiple uniquely tuned, energized marker assemblies 14 may be reliably and uniquely measured by the sensor array 16. The unique marker assemblies 14 at unique resonant frequencies may be excited and measured simultaneously or during unique time periods. The signal from the tuned miniature marker assembly 14 is significantly above environmental signal noise and sufficiently strong to allow the signal processor 28 (FIG. 1) to determine the marker assembly's identity, precise location, and orientation in three dimensional space relative to the sensor array 16 or other selected reference frame.

The system 10 of the illustrated embodiment in FIG. 1 can be used in many different applications in which the miniature marker's precise three-dimensional location within an accuracy of approximately 1 mm can be uniquely identified within a relatively large navigational volume, such as a volume of 12 cm×12 cm×12 cm or greater. One such application is the use of the system 10 to accurately track the position of targets (e.g., tissue) within the human body. In this application, the leadless marker assemblies 14 are implanted at or near the target so the marker assemblies move with the target as a unit and provide positional references of the target relative to a reference frame outside of the body. Such a system could also track relative positions of therapeutic devices (i.e., surgical tools, tissue ablation devices, radiation delivery devices, or other medical devices) relative to the same fixed reference frame by positioning additional leadless marker assemblies 14 on these devices at known locations or by positioning these devices relative to the reference frame. The size of the leadless markers used on therapeutic devices may be increased to allow for greater marker signal levels and a corresponding increase in navigational volume for these devices.

The system 10 is configured to generate a sufficient source excitation magnetic field signal, as an example, source excitation coil Magnetic Dipole Moment approximately greater than 0.5 $A*m^2$, at the appropriate frequency to energize the one or more marker assemblies significantly above the environmental background noise. The system 10 also generates excitation source magnetic field flux signals at orthogonal spatial orientations (e.g., along the X, Y and Z axes) to excite a marker assembly 14 that may be a resonator having a single coil substantially oriented along a single axis and spatially orthogonal to excitation energy along the other two axes. The system 10 can also be configured to generate excitation source magnetic field flux signals at variable frequencies to energize a plurality of marker assemblies 14 that contain resonant circuits tuned to these unique frequencies. Accordingly, the multiple marker assemblies 14 can be sequentially or simultaneously energized.

The system 10 is also configured to avoid the difficult process of separating the small marker signal 22 from the much more powerful source excitation signal 20 by measuring the marker signal during a time period when the source signal is substantially not present. The residual source excitation signal 20 can cause substantially less accurate results in the location determination if not controlled. The system 10 provides for the measurement of the marker signal 22 with a sufficient number of spatially distributed sensors 26 at a sufficient signal-to-noise ratio so that an inversion algorithm provided in the signal processor 28 can accurately solve for the three-dimensional location of the particular marker assembly 14 relative to the known reference frame of the sensor array 16.

Figure 3:
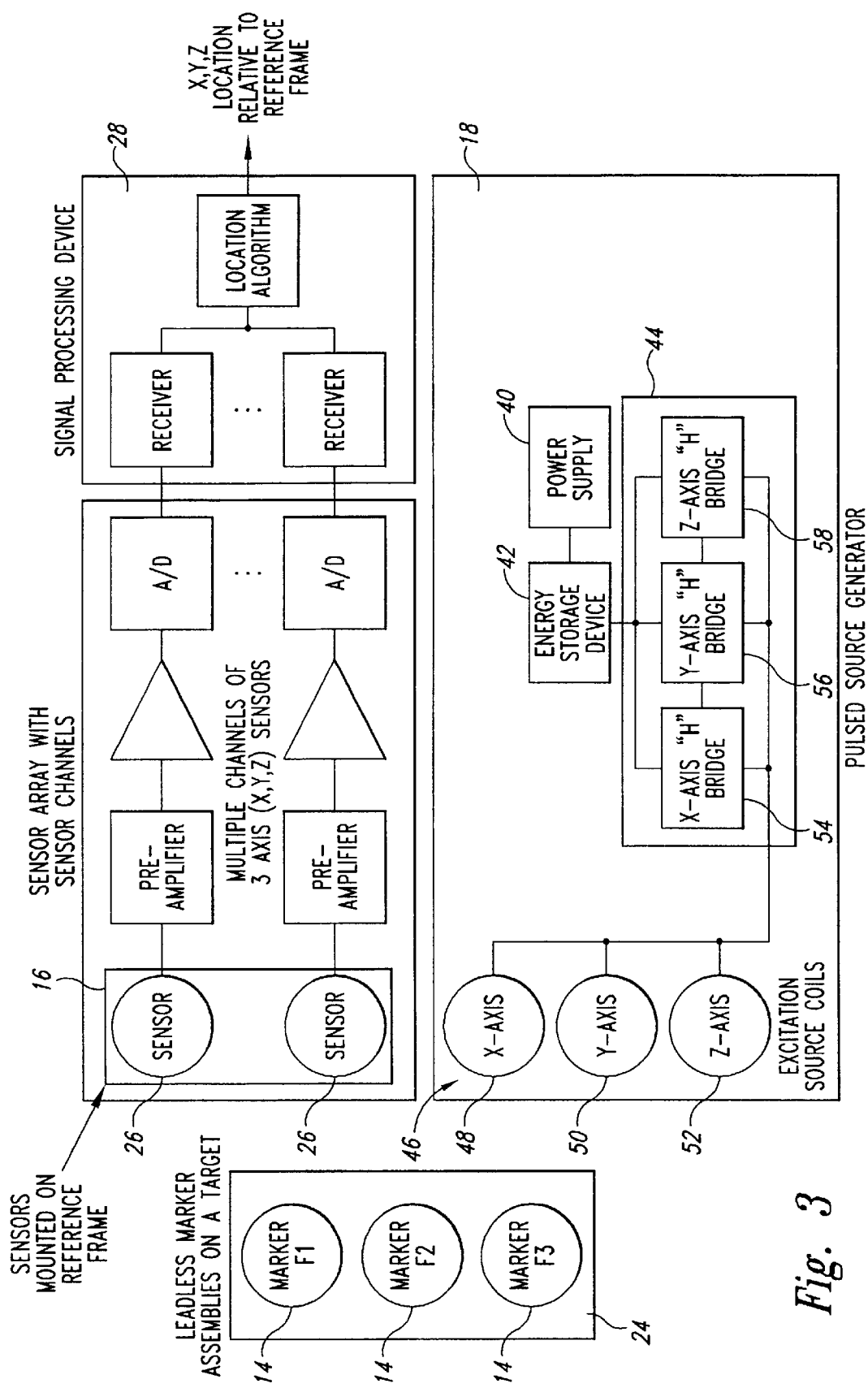
FIG. 3 is a schematic block diagram of the pulse excitation system of FIG. 1 illustrating a pulsed generator, a signal processing device, a sensor array, and leadless markers.

FIG. 3 is a schematic block diagram of the system 10 in accordance with one embodiment. As seen in FIG. 3, the plurality of leadless miniature marker assemblies 14 on the target 24 are remote from the pulsed source generator 18 and from the sensor array 16. The sensor array 16 is operatively coupled to the signal processing device 28.

The pulsed source generator 18 includes a high voltage power supply 40 coupled to an energy storage device 42. In one embodiment, the power supply 40 is a 500-volt power supply, although other power supplies with higher or lower voltages can be used. The energy storage device 42 in one embodiment is a high voltage capacitor that can be charged and maintained at a relatively constant charge by the power supply 40. Energy stored in the storage device 42 allows for providing energy to and removing energy from the source coil inductor. A small amount of stored energy is present in the source coil inductor at maximum current relative to the energy stored in the energy storage device 42.

The energy storage device 42 is capable of storing adequate energy to minimize voltage drop in the energy storage device while having a low series resistance so as to minimize power losses. The energy storage device 42 also has a low series inductance to allow for maximum source generator excitation capability to drive the source coil 46. Specialized aluminum electrolytic capacitors used in flash energy applications may be used in one of the embodiments of system 10. Alternative energy storage devices can also include NiCd and lead acid batteries, as well as alternative capacitor types, such as tantalum, film, or the like.

The pulsed source generator 18 of the illustrated embodiment also includes a switching network 44 coupled between the energy storage device 42 and a plurality of source coils 46. The switching network 44 is configured to control the polarity of the voltage across the source coils 46 and the resultant current magnitude and polarity with time through the source coils so that the source coils 46 each generate the high energy excitation field 20 for activating the marker assemblies (FIG. 1).

In the illustrated embodiment, the excitation source coils 46 includes three coils orthogonally oriented to correspond to the X, Y, and Z axes of a selected frame of reference. The three coils will be referred to herein as the X coil 48, Y coil 50, and Z coil 52, each of which is configured to provide a magnetic field flux signal along the respective X, Y, and Z axes. The X, Y, and Z coils 48, 50, and 52 with their orthogonal orientation effectively avoid blind spots for excitation of marker assemblies 14 and can allow the marker assemblies to be in any orientation relative to the pulsed source generator 18 and still be highly energized upon activation of the excitation source coils 46.

The source coil 46 in the illustrated embodiment is configured to deliver adequate source excitation magnetic fields, which is defined by the area, number of turns, current, and other characteristics of the coil. The source coil 46 is constructed with conductors designed to minimize power loss due to resistive losses as well as resistive losses due to skin effects. Examples include small diameter wire wound in a LITZ wire configuration to minimize skin effects, or alternatively, a thin sheet of conductor to minimize skin effects. Parasitic interwinding capacitance of the source coil inductor and interconnection conductors should also be minimized to reduce unintended coil current spikes due to very short switching network voltage transition times and other unintended source coil resonant circuit effects.

The switching network 44 in the illustrated embodiment includes a plurality of switches that control energy flow to the X, Y, and Z coils 48, 50 and 52 These switches include X-switches 54 coupled to the X-coil 48, Y-switches 56 coupled to the Y-coil 50, and Z-switches 58 coupled to the Z-coil 52. The X-switches 54 include a plurality of activatable switch mechanisms that control the polarity of the voltage across the X-coil 48 so as to control the polarity of the derivative with time of the current flow through the X-coil. The Y-switches 56 control the polarity of the voltage across the Y-coil 50 so as to control the polarity of the derivative with time of the current flow through the Y-coil. Similarly, the Z-switches 58 are configured to control the polarity of the voltage across the Z-coil 52 so as to control the derivative with time of the current flow through the Z-coil. The derivative with time of the current flow at a particular voltage polarity across a particular source coil results in either an increasing or decreasing current ramp with time through the source coil.

In the illustrated embodiment, each of the X, Y, and Z switches 54, 56, and 58 have an H-bridge configuration with four switch mechanisms controlled to selectively direct electrical current through the respective X, Y, or Z coil 48, 50, and 52, thereby generating a pulsed magnetic field from the respective source coil.

The X, Y, and Z switches 50, 56, and 58 are also each configured to alternately switch between first and second "on" positions to generate a current flow with a bipolar waveform. In the first "on" position, the current flow in one has a continually increasing current ramp with time through the respective X, Y, or Z coil 48, 50 or 52 to generate the magnetic excitation field. In the second "on" position, the current flow has a continually decreasing current ramp with time through the respective X, Y, or Z coil 48, 50 or 52 to generate the magnetic excitation field. Such alternate switching over the pulse waveform period effectively provides for alternating the polarity of the current flow from a positive polarity to a negative polarity. The X, Y, and Z switches 54, 56, and 58 are also configured to alternately transfer stored energy from the energy storage device 42 to the respective X, Y, or Z axis source coil 48, 50, or 52 and to transfer the stored energy from the respective source coil back to the energy storage device when alternating switching between the first and second "on" positions.

The X, Y, and Z switches 54, 56, and 58 are also configured to move to an "off" position to prevent energy transfer from the energy storage device 42 to the respective X, Y, or Z coils 48, 50, or 52. Once the X, Y, or Z switch 54, 56, or 58 is switched to the "off" position at the appropriate time when the energy (i.e. the current) in the source coil is substantially zero, the respective X, Y, or Z coil 48, 50, or 52 no longer generates a magnetic field such that the pulsed excitation signal 20 ceases, so only the marker signal 22 emanates from the marker assembly 14 is measurable.

The alternating current flow through the X, Y, or Z coil 48, 50, or 52 generates the pulsed magnetic field in the selected axis to excite the marker assembly 14 located at a determinable distance from the coil. The following is an equation for calculation of the magnetic field excitation at a distance from a source coil inductor of a solenoid shape:

$$B_{marker}(\text{distance}) = \frac{\mu_0 \cdot I_{source} \cdot r_{source}^2 \cdot N_{source}}{2 \cdot (r_{source}^2 \cdot \text{Distance}^2)^{\frac{3}{2}}}$$

Where:

$B_{marker}$(distance)=magnetic field flux density at a distance from the source coil along the coil axis $\mu_o$=permeability of free space between the source coil and the marker assembly $r_{source}$=Radius of the source coil (meters)

$N_{source}$=Number of turns of wire around the source coil

Distance=distance from the source coil (meters)

$I_{source}$=Electrical current through source coil (amperes)

The electrical current ($I_{source}$) through the X, Y, or Z coil 48, 50, or 52 is determined by the voltage applied across the coil inductance (L). The inductance (L) of an air core coil (solenoid) is approximated by:

$$L = \frac{(\mu_o \cdot \pi \cdot r_{source}^2 \cdot N_{source}^2)}{length_{source}}$$

Where:

L=Inductance of the source coil $\mu_o$=permeability of free space $r_{source}$=Radius of the source coil (meters)

$N_{source}$=Number of turns of wire around the source coil length$_{source}$=Length of source coil (meters)

The inductance of the source coil determines the electrical current derivative with time through source coil inductor as follows:

$$V=L*dI/dt \text{ or } V/L=dI/dt$$

Where:

V=voltage potential across the coil (volts)

L=Inductance of the source coil dI/dt=The change in coil current with time

To efficiently transfer energy to a coil and create the magnetic excitation field, power losses due to resistance in the source coil circuit should be minimized. The power (i.e., RMS power) in the system is determined as follows:

$$P=I^2 R_{TOTAL}$$

Where:

I=Root Mean Square value of the current $R_{TOTAL}$=Total resistance in the source coil circuit The power losses of the system 10 limits the strength of the magnetic excitation field that the system is capable of delivering. The strength of the magnetic excitation field decreases with the cube of the distance from the magnetic field source (e.g., the source coil 46). Furthermore, the magnetic excitation field increases linearly with current, but the power dissipation in the system increases as the square of the current. Accordingly, the requirements for source drive electronics become more challenging to allow for adequate levels of the marker signal 22 as the magnetic excitation field requirements increase.

In one embodiment, the source coil 46 can be operated as a tuned circuit wherein the source coil inductor is tuned with a capacitor chosen for the desired resonant frequency of the marker assembly 14. The reactance of the inductor is equal to and opposite the capacitor at the frequency of interest, such that only the resistance of the source coil circuit is seen by the drive electronics. Substantial stored energy can occur in the tuned circuit, however, that may limit the time in which the source coil excitation signal is shutoff. Longer shut-off time reduces the time during which the marker resonator signal can be measured effectively in the absence of the source signal. Accordingly, a shorter shutoff time can be very desirable. A shorter shutoff time also allows for adequate marker ring down signal to remain after the source signal has decayed such that the marker signal may be measured at a sufficient signal to noise ratio for accurate location of the marker.

The system 10 of the one embodiment provides an untuned source coil 46 configured to excite the leadless marker assembly's resonator with the pulsed excitation signal 20 having a high level of source excitation energy. The system 10 also provides a very short source excitation turnoff time to achieve optimal performance for measuring the marker signal 22 after the source excitation signal 20 is significantly extinguished. Accordingly, the turnoff time for an untuned source coil can have a significant impact on the effectiveness of the system 10, so the system is configured to have only limited stored energy after turnoff time.

Therefore, the pulsed source generator 18 of the system 10 is configured to deliver high source coil current amplitudes at the optimal marker excitation frequencies to energize the leadless markers 14 before the time decaying marker ring down signal is measured.

Figure 4:
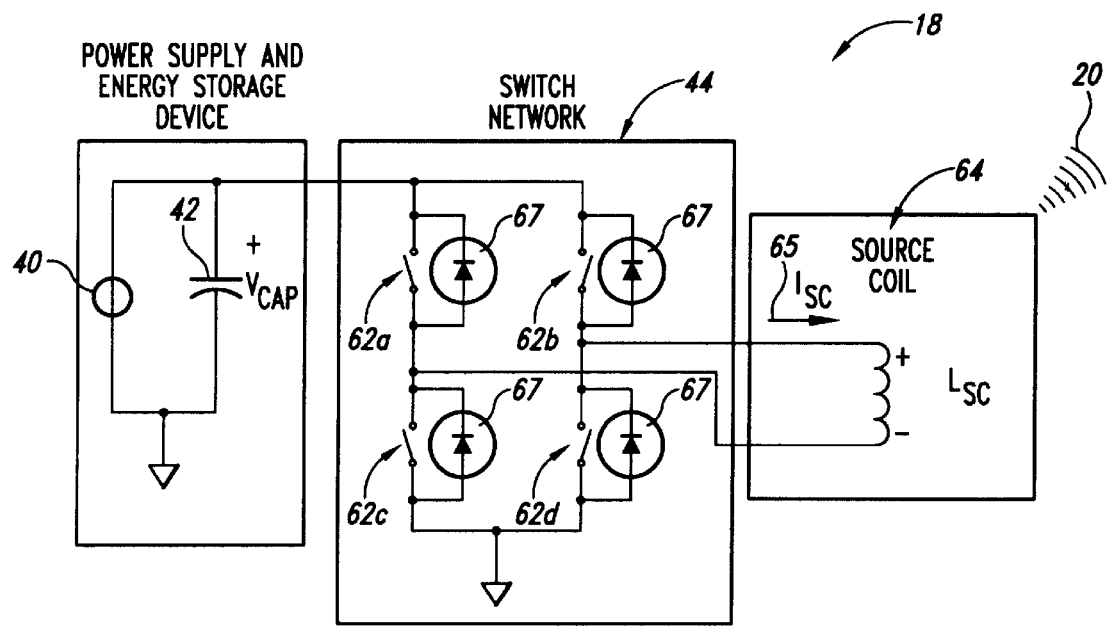
FIG. 4 is a schematic block diagram of an embodiment of the pulsed source generator of FIG. 3.

FIG. 4 is a schematic block diagram of a pulsed source generator 18 of one embodiment. In this illustrated embodiment, a high-voltage power supply 40 and energy storage device 42 are shown coupled to a single switch network 44, which has a single H-bridge switching configuration. This switch network 44 has four switches 62a–d coupled together so as to control the current flow to a single source coil 64. In this embodiment, when multiple source coils are used, each source coil is coupled to a separate switch network, power supply, and energy storage device. In one embodiment, a common energy storage device and a common power supply for multiple switching networks and corresponding source coils are used.

The switch network 44 of the illustrated embodiment with the H-bridge configuration constructed of MOSFET devices. The switching devices have a low "on" series of resistance (less than or equal to approximately 1 ohm) to minimize power losses. Furthermore, very short switching times (less than approximately 25 nanoseconds) are provided to minimize switching induced power losses and maximum excitation delivery. The short switching times allow for high frequency system operation (for example, 50–600 kHz) that improves overall system performance due to increases in inductive coupling efficiencies between the source, marker, and sensor coils with frequency. Alternate embodiments have switch networks 44 that include one-half H-bridge configurations (having only two switches) with a matched set of power supplies and two matched energy storage devices configured to deliver a bipolar voltage drive to the source coil 46. The alternative switching components can include bipolar junction transistors (BJT), JFETS, and various possible vacuum tube configurations.

The power supply 40 directs charge to and maintains a relatively constant energy storage level at the energy storage device 42 by delivering average power to the energy storage device. The amplitude of the charging current is large enough to compensate for average power consumption in the pulse generator and keep the energy storage device at a relatively constant voltage. The energy storage capacitor must be large enough to minimize voltage drop during pulse generation and capable of both supplying high instantaneous power to the switch network and returning high instantaneous power from the switch network 44. The following example for one embodiment has equations for both calculation of the power supply average power and pulse generator instantaneous power delivery:

| | |
|---|---|
| $V_{cap}$ = 500 V | Capacitor charge voltage |
| $R_{switching}$ = 2.0 ohm | Total resistance in "on" state (2 switches closed at a time) |
| $R_{coil}$ = 0.25 ohm | Source coil resistance |
| $R_{energy\_storage\_device}$ = 0.05 ohm | Energy storage device resistance |
| $I_L$(rms) = 4.8 amps | Source coil rms current |
| Duty cycle = 50% | % of time generator is pulsing |
| Average power dissipation = * Duty cycle | $(R_{switching} + R_{coil} + R_{energy\_storage\_device}) * I_L(rms)^2$ |
| $P_{Power\_supply}$ (average) = | $(2 + 0.25 + 0.05) * (4.8)^2 * 0.5$ Watts |
| $P_{Power\_supply}$ (average) = | 26 watts |
| $P_{instantaneous}$ (during pulsing) = | 500 V * 4.8 amps RMS = 2,400 VA RMS |

To maintain constant energy storage:

$I_{power\ supply}$ (average)=$P_{Power\_supply}$ (average)/$V_{cap}$ $I_{power\_supply}$ (average)=26W/500V=52milli Ampere The switch network 44 is configured so pairs of the switches 62a–d are opened and closed simultaneously when the other pair of switches are simultaneously closed and opened. As a result, the switch network 44 is configured to control the voltage across the source coil 64 in alternating polarities. As a result, the current flow through the source coil 64 alternates between positive and negative polarity over the pulsed magnetic excitation signal waveform pulse burst time period. This alternating of the current flow through the source coil between positive and negative polarity results in the pulsed magnetic excitation signal 20 from the source coil.

In one embodiment, the switch network 44 moves between the first "on" position when switches 62b and 62c are closed and switches 62a and 62d are open, and the second "on" position when switches 62b and 62c are open and switches 62a and 62d are closed. In this first "on" position, the voltage having a positive direction across the source coil 64 increases the current over the pulse "on" time through the source coil in the direction of arrow 65. In the second "on" position, the voltage having a negative direction across the source coil 64 decreases the current over the pulse "on" time through the source coil in the opposite direction of arrow 65. The resulting pulsed excitation signal due to multiple pulses over the pulse burst time period and the repetition frequency of the pulse burst has determinable frequency components corresponding to the resonant frequencies of the marker assemblies 14 for activation of the markers (not shown).

The switch network 44 also includes an "off" position that opens the circuit to prevent the current from flowing to the source coil. Accordingly, no magnetic field is generated and no pulsed excitation signal 20 is emanated from the source coil 64. The switch network 44 can be switched to the "off" position by opening switches 62a and 62b and by turning 62c and 62d to a closed position to shunt the source coil which allows for exponential decay of residual energy in the source coil. The current then circulates through one of the two switches 62c and 62d and one of two H-bridge protection diodes 67 coupled to the switches depending on the polarity of the residual current. The residual current in the source coil decays by the following exponential time constant:

$$\tau = L_{sc}/(R_L + R_{switch} + R_{protection\_diode})$$

where:

$L_{sc}$=Source coil inductance $R_L$=Source coil resistance $R_{switch}$=Switch "on" resistance $R_{protection\_diode}$=Protection diode "on" resistance As a result, the switch network 44 is controllable to control the pulsed excitation signal 20 and can be switched to the "off" position to terminate the excitation signal after the marker assemblies have been sufficiently energized. When the excitation signal is off, the marker signals 22 do not have to be distinguished from the excitation signal 20 when the marker signal is being measured and analyzed as discussed above.

In an alternate embodiment, the switch network 44 can be switched to the "off" position by opening all switches 62a–d. However, care must be taken to assure that little residual energy remains in the source coil 64 at the time all switches are turned "off", otherwise inductive kick back induced voltage spikes due to an instantaneous current change through the inductor with time may damage the switch network or result in undesired oscillations of the residual current in the source coil.

Figure 5:
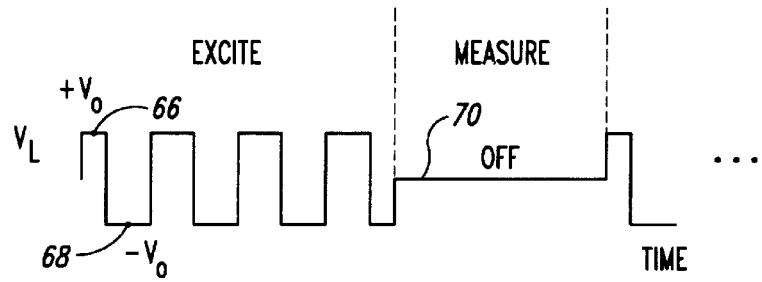
FIG. 5 is a schematic voltage diagram showing the voltage across a source coil of the system of FIG. 1 during excitation "on" and excitation "off" phases over time for the pulsed excitation and location of the marker assembly.

FIG. 5 is a schematic voltage diagram showing the bipolar voltage across a source coil 64 to generate the pulsed excitation signal. The voltage is controlled by activating the switch network 44, as discussed above with respect to FIG. 4. When the switch network 44 is switched to the first "on" position, the voltage across the source coil 64 is positive as shown in FIG. 5 at reference number 66, thereby providing a positive polarity. When the switch network 44 is switched to the second "on" position, the voltage across the source coil 64 shifts and is negative as shown in FIG. 5 at reference number 68, thereby providing a negative polarity.

The switch network 44 (FIG. 4) alternates between the first and second "on" positions so as to alternate the voltage across the source coil 64 between the positive and negative polarities. When the switch network 44 is switched to the first "on" position, energy is drawn from the capacitor 42 toward the source coil 64. When the switch network 44 is switched to the second "on" position, energy is directed back to the capacitor 42 until the time when the current changes polarity and then energy is again drawn from the capacitor. When the switch network 44 is switched back to the first "on" position, then energy is again directed back to the capacitor 42 until the time when the current changes polarity again and then energy is again drawn from the capacitor. As a result, the switching network 44 is configured to alternately transfer stored energy from the energy storage device 42 to the source coil 64 and to transfer the storage energy from the source coil back to the energy storage device when alternately switching between the first and second "on" positions.

In one embodiment, the switch network 44 is configured so that the switches 62a–d (FIG. 4) are in the first "on" position for the same total time period for a particular pulse burst that they are in the second "on" position. Accordingly, the time period at the positive polarity is the same time period as the negative polarity for the voltage across the source coil 64. When the switch network 44 is switched to the "off" position, the voltage across the source coil 64 is zero, as reflected at reference 70 in the voltage diagram. When the current through the source coil 64 (FIG. 4) is zero, the source coil provides no excitation signal 20 that would interfere with the marker signal 22 generated by the marker assembly 14 as discussed above. Accordingly, the switch network 44 is in the "off" position during the measurement phase when the marker signal 22 is detected and measured for determining the marker assembly's location in three dimensional space.

Figure 6:
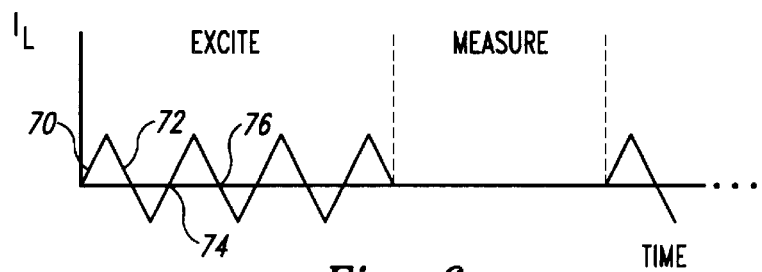
FIG. 6 is a schematic bipolar current diagram during the excitation "on" and excitation "off" phases over time of FIG. 5 for pulsed excitation and location of a marker assembly.

FIG. 6 is a schematic bipolar current diagram corresponding to the voltage diagram of FIG. 5. Referring to FIGS. 4, 5 and 6, when the switch network 44 (FIG. 4) is in the first "on" position corresponding so the voltage has a positive polarity 66 (FIG. 5), the current flow through the source coil 64 (FIG. 4) has a continually increasing current ramp 70 (FIG. 6) so as to generate the magnetic excitation field 20 with the positive polarity. When the switch network 44 (FIG. 4) is in the second "on" position corresponding to the negative polarity 68 (FIG. 5), the current flow has a continually decreasing current ramp 72 (FIG. 6). When the switch network 44 switches back to the first "on" position, the current flow switches back to an increasing current ramp 70. Accordingly, the current flow has a bipolar, generally non-sinusoidal triangular shaped waveform.

As seen in FIG. 6, when the current flow switches directions, for example from the decreasing current ramp 72 to the increasing current ramp 70, there is a point shown at 74 at which the current in the source coil is substantially at zero amps. Similarly, when the current flow has the decreasing current ramp 72, there is a point shown at 76 at which the current in the source coil 64 (FIG. 4) is at zero amps. The switch network 44 is configured to switch to the "off" position when the current flow through the source coil 64 is substantially at these zero points 74 and 76, and thus at zero amps. When the current in the source coil 64 approaches zero amps, the signal decay time for the pulsed excitation signal 20 approaches zero, such that the pulsed excitation signal is substantially instantaneously shut off so as to provide no interference with the marker signal 22 generated by the energized marker assembly 14.

When the switch network 44 is switched to the "off" position, the extent of signal decay over time of the source coil 64 current is a function of the resistance in the switch network as well as resistance and inductance in the source coil circuitry. In the illustrated embodiment, the switch network 44 and source coil 64 are configured such that when the switch network is switched to the "off" position, any pulsed excitation signal 20 from the source coil is immeasurable within approximately one cycle of the energized marker assembly. Therefore, the sensor array 16 (FIG. 1) and the signal processor 28 are configured to begin measuring the marker signal 22 after one cycle of the marker assemblies 14.

Figure 7:
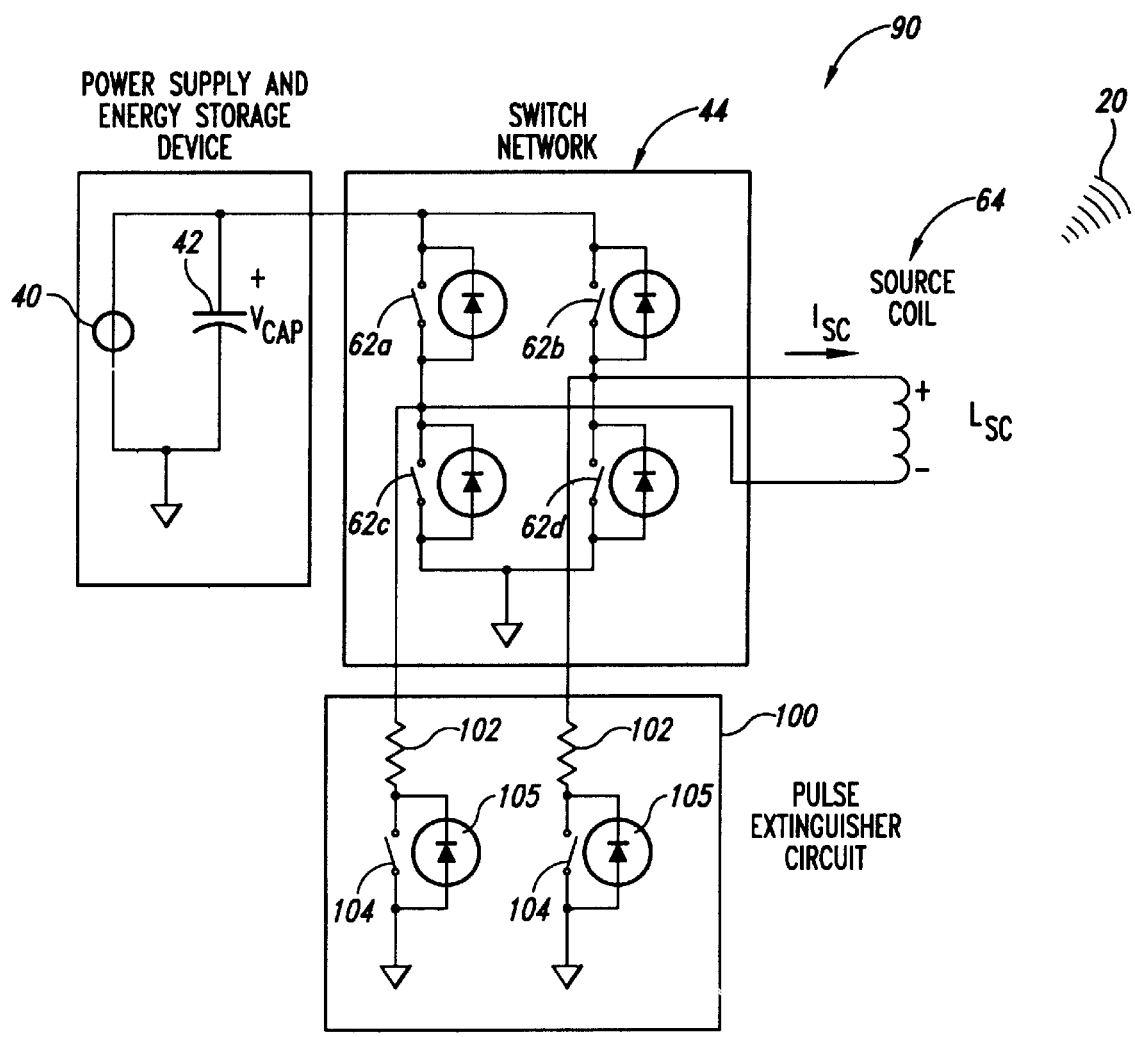
FIG. 7 is a schematic electrical diagram of an alternate embodiment of the system of FIG. 3, the system including a pulse extinguishing circuit.

FIG. 7 is a block diagram of a pulsed source generator 90 having a pulse extinguisher circuit 100 therein in accordance with an alternate embodiment. In this alternate embodiment, the pulsed source generator 90 includes the power supply 40 and the energy storage device 42 coupled to the switch network 44 similar to the embodiments discussed above. The switch network 44 is also coupled to the source coil 64. The switch network 44 is also connected to the pulse extinguisher circuit 100 in parallel with the source coil inductor, such that the pulse extinguisher circuit does not conduct current during pulse generation. The pulsed source generator 90 of this alternate embodiment provides the switch network 44 moveable between the first "on" position, the second "on" position as discussed above, and an "off" position where all of the switches, 62a–62d, are opened. When the switch network 44 is switched to the "off" position, the pulse extinguisher circuit 100 switches 104 are closed to quickly dissipate the residual energy in the source coil 64 so as to limit the time that an excitation field continues to be generated after the switch network has been moved to the "off" position.

The pulse extinguisher circuit 100 is configured to include a pair of resistors 102 and switches 104 that can be activated to quickly dissipate the residual energy in the source coil when the circuit is closed and to interrupt the current flow through the extinguisher circuit when the switches 104 are open during excitation pulse generation. At the end of a pulse burst, the residual source coil current is conducted through one of the two switches 104, one of the two resistors 102 and an H-bridge protection diode 105, depending on the polarity of the residual current. Pairs of switches 104 and resistors 102 are provided so the residual current may be either of a positive or negative polarity. The time constant for de-energizing the source coil inductor is determined by the following equation:

$$\tau = L_{sc}/(R_L + R_{switch} + R_{protection\_diode} + R_{pulse\_extinguisher})$$

Where:
$L_{sc}$ = Source coil inductance
$R_L$ = Source coil resistance
$R_{switch}$ = Switch "on" resistance
$R_{protection\_diode}$ = Protection diode "on" resistance
$R_{pulse\_extinguisher}$ = Pulse extinguisher resistor resistance The pulse extinguisher circuit's resistors 102 decrease the exponential decay time constant of residual current in the source coil by adding additional resistance to the source coil circuit only during turnoff time. As a result, the pulse extinguisher circuit 100 decreases the turnoff time of the source generator and does not decrease the overall energy efficiency or power dissipation of the pulsed source generator 90.

In the illustrated embodiment, the pulse extinguisher circuit 100 is configured so that no measurable or detectable excitation field remains after the switch network 44 has been moved to the "off" position within less than one cycle of the resonating marker assembly 14 (FIG. 1). Accordingly, the pulse extinguisher circuit 100 facilitates the termination of the pulsed excitation signal 20 so that the resonating marker assembly 14 can be easily detectable and located with the signal processing assembly 28 to accurately identify the three-dimensional location of the resonating marker assembly relative to the sensor array 16.

While the pulse extinguisher circuit 100 is defined in the illustrated embodiment as providing the resistors 102 and switches 104, with additional protection diodes 105, other pulse extinguisher circuits can be used so as to increase the resistance of the total source coil circuit when the switch network is in the "off" position. The alternate pulse extinguisher circuits should not increase system power dissipation and decrease energy efficiency by adding additional switch resistance during pulse delivery because of its presence.

Although specific embodiments of, and examples for, the present invention are described herein for illustrative purposes, various equivalent modifications can be made without departing from the spirit and scope of the invention, as will be recognized by those skilled in the relevant art. The teachings provided herein of the present invention can be applied to systems for excitation of leadless miniature markers, not necessarily the exemplary system generally described above.

From the foregoing it will be appreciated that, although specific embodiments of the invention have been described herein for purposes of illustration, various modifications may be made without deviating from the spirit and scope of the invention. Accordingly, the invention is not limited except as by the appended claims.

I claim:

1. A system for generating a pulsed excitation field for excitation of a leadless marker assembly in or on a body, comprising:
   an energy storage device;
   a source coil configured to deliver a pulsed magnetic excitation signal to the leadless marker assembly, said pulsed magnetic excitation signal being of sufficient strength and of sufficiently limited duration to cause the leadless marker assembly to generate a marker signal that is measurable outside of the body; and
   a switching network coupled to the energy storage device and the source coil wherein the switching network is configured to alternately transfer stored energy from the energy storage device to the source coil and to transfer energy from the source coil back to the energy storage device.

2. The system of claim 1 wherein the pulsed magnetic excitation field source signal has a generally triangular-shaped bipolar waveform having a positive and negative polarity.

3. The system of claim 1 wherein the pulsed magnetic excitation signal has a generally triangular-shaped unipolar waveform having only a single polarity.

4. The system of claim 1 wherein the pulsed magnetic excitation signal has a non-sinusoidal waveform having a positive and negative polarity.

5. The system of claim 1 wherein the energy storage device is a capacitor.

6. The system of claim 1 wherein the switching network includes at least two switches configured to switch voltage across the source coil between a positive voltage polarity and a negative voltage polarity.

7. The system of claim 1 wherein the switching network includes a first H-bridge.

8. The system of claim 1 wherein the switching network includes a first H-bridge configured to switch voltage across the source coil between a positive voltage polarity and a negative voltage polarity.

9. The system of claim 1 wherein the electrical current directed through the source coil has a generally triangular-shaped waveform, and the switching network includes a first H-bridge configured to cyclically switch voltage across the source coil between a positive polarity and a negative polarity.

10. The system of claim 1, further comprising a power supply that delivers electrical current to energize the energy storage device, and the switching network is configured so the electrical current cycles between having a positive polarity and a negative polarity to provide signal pulse bursts, and in each signal pulse burst the electrical current has a positive polarity and a negative polarity for substantially the same period of time.

11. The system of claim 1 wherein the switching network is configured to move to the off position when electrical current in the switching network is at approximately zero amps.

12. The system of claim 1, further comprising a leadless resonating marker remote from the source coil, and being excitable by the pulsed magnetic excitation signal to generate a marker resonant signal with selected frequency components.

13. The system of claim 12 wherein the switching network is configured to substantially prevent the source coil from generating any excitation signal within one cycle or less of the marker resonant signal.

14. The system of claim 12, further comprising a plurality of sensors configured to measure signals from the leadless marker assembly upon excitation by the pulsed magnetic excitation signal.

15. The system of claim 1, further comprising a pulse extinguisher circuit coupled to the switching network and configured to reduce the time constant of the residual source signal decay of the pulsed magnetic excitation signal.

16. The system of claim 1 further comprising a marker signal location system.

17. The system of claim 1 wherein the pulsed magnetic excitation signal is a programmable pulse burst duration magnetic excitation signal.

18. The system of claim 1 wherein the pulsed magnetic excitation signal is a programmable pulse repetition frequency magnetic excitation signal.

19. The system of claim 1 wherein the switching network and the source coil are a first switch network and first source coil, respectively, that generate a first source signal in a first spatial orientation, and further comprising a second switch network and a second source coil that generate a second source signal in a second spatial orientation different than the first spatial orientation.

20. The system of claim 19, further including a third switch network and third source coil that generate a third source signal in a third spatial orientation different than the first and second spatial orientations.

21. The system of claim 19, further comprising a power supply that is configured to deliver power to energize an energy storage device, and the switching network is configured to:
   direct electrical current through the source coil to generate a pulsed magnetic excitation field;
   alternately switch between a first on position and a second on position to generate the pulsed magnetic field from the source coil;
   switch to an off position to prevent energy transfer from the energy storage device to the source coil; and
   alternately transfer stored energy from the energy storage device to the source coil and transfer stored energy from the source coil back to the energy storage device.

22. The system of claim 21 wherein the switching network and the source coil are a first switch network and first source coil that generate a first source signal in a first spatial location, and further comprising a second switch network and a second source coil that generate a second source signal in a second spatial location different than the first spatial location.

23. The system of claim 22, further including a third switch network and a third source coil that generates a third source signal in a third spatial location different than the first and second spatial location.

24. A method of energizing a leadless marker assembly, comprising:
   storing electrical energy in an energy storage device;
   directing the energy from the energy storage device through a polarity switching mechanism to alternately transfer stored energy from the energy storage device to a source coil and to transfer energy from the source coil back to the energy storage device by alternately switching between first and second on positions;
   directing the electrical energy from the switching mechanism through the source coil to generate a magnetic field;
   energizing a leadless resonating marker assembly with the magnetic field.

25. The method of claim 24 wherein the magnetic field source signal is a non-sinusoidal waveform having both a positive and negative polarity.

26. The method of claim 24 wherein the waveform frequencies of the magnetic field are adjusted to excite multiple markers of unique resonant frequencies.

27. The method of claim 24 wherein the waveform frequencies of the magnetic field are adjusted to excite a first marker substantially at the first marker resonant frequency.

* * * * *